US006146901A

United States Patent [19]

Carver et al.

[11] Patent Number: 6,146,901

[45] **Date of Patent: *Nov. 14, 2000**

[54] COMPOSITION FOR MANIPULATING OPTICAL AND ELECTRICAL PROPERTIES OF PARTICLES TO ACHIEVE TARGET VALUES FOR SUCH PROPERTIES AND METHODS FOR USING THE COMPOSITION

[75] Inventors: Franklin J. Carver, Miami, Fla.; James D. Lapicola, Lafayette; Lorraine A. Granier, San Ramon, both of Calif.

[73] Assignee: Hematronix, Inc., Plano, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/876,973

[22] Filed: Jun. 16, 1997

[51] Int. Cl.[7] .......................... G01N 33/48; G01N 33/49

[52] U.S. Cl. ................................ 436/174; 436/8; 436/10; 436/17; 436/18; 436/63; 436/176

[58] Field of Search .................................. 436/8, 10, 17, 436/18, 63, 174, 176; 252/408.1

[56] References Cited

U.S. PATENT DOCUMENTS

| | | |
|---|---|---|
| 3,741,875 | 6/1973 | Ansley et al. . |
| 3,873,467 | 3/1975 | Hunt . |
| 4,198,206 | 4/1980 | Ryan . |
| 4,199,471 | 4/1980 | Louderback et al. . |
| 4,219,440 | 8/1980 | Runck et al. . |
| 4,324,686 | 4/1982 | Mundschenk . |
| 4,358,394 | 11/1982 | Crews et al. . |
| 4,390,632 | 6/1983 | Carter, II . |
| 4,436,821 | 3/1984 | Ryan . |
| 4,485,175 | 11/1984 | Ledis et al. . |
| 4,579,824 | 4/1986 | Louderback et al. . |
| 4,698,312 | 10/1987 | Wong et al. . |
| 4,704,364 | 11/1987 | Carver et al. . |
| 4,751,179 | 6/1988 | Ledis et al. . |
| 4,777,139 | 10/1988 | Wong et al. . |
| 5,320,964 | 6/1994 | Young et al. . |
| 5,380,664 | 1/1995 | Carver et al. . |
| 5,512,485 | 4/1996 | Young et al. . |

*Primary Examiner*—Jan Ludlow
*Attorney, Agent, or Firm*—Shook, Hardy & Bacon L.L.P.

[57] ABSTRACT

A composition and a method for using the composition for manipulating the electronic and optical properties of biological particles are disclosed. The composition generally has a hypotonic buffering solution, a polyhydroxy alcohol, a stabilizing agent, and, in some applications, a non-ionic surfactant. By varying the relative concentrations of these components and by adjusting the timing of their combination and interaction, the composition and method allow for the alteration of the electronic and optical properties of the particles to achieve target values for the properties. In one particularly advantageous application, the composition and method of the invention allow for the creation of selected analogs for the subpopulations of human leukocytes from a single biological particle for use as a control product in differentiating particle analyzers.

58 Claims, No Drawings

COMPOSITION FOR MANIPULATING OPTICAL AND ELECTRICAL PROPERTIES OF PARTICLES TO ACHIEVE TARGET VALUES FOR SUCH PROPERTIES AND METHODS FOR USING THE COMPOSITION

BACKGROUND OF THE INVENTION

This invention relates to the analysis of particles and, more particularly, to a composition for manipulating the optical and electrical properties of particles for subsequent analysis by selected measuring devices and a method for using the composition.

It has become axiomatic in the field of medical science that the diagnosis and treatment of disease and illness must be predicated on a precise analysis of the patient's biological systems. The respiratory, circulatory, immune and nervous systems contribute to the overall well-being of a person and, if any one of these systems is compromised by a foreign organism, such as a virus or bacterial agent, serious health consequences may result. One way of ascertaining the health of a system is to evaluate its constituent biological particles, such as its red blood cells, white blood cells, antibodies and platelets. The information revealed by the examination of these constituent biological particles is invaluable to the physician or lab technician in assessing the status of the overall system and, thus, determining the cause of illness or disease.

The analysis of biological particles requires a detailed examination of the individual properties of the particles. Even slight deviations in the values of certain properties are sufficient to allow the diagnosis and treatment of disease and illness at very early stages of progression. It is therefore critical to obtain the highest degree of accuracy and reliability in the measurements of those properties so that an effective course of treatment can be planned.

The technology for analysis of biological particles has advanced dramatically over recent years. Direct current electronic particle counters are among these advancements. These instruments determine the size and volume of biological particles by measuring the electrical resistance of the particle relative to its surrounding fluid. Some electronic particle analyzers utilize radio frequency to measure the composition and nature of the material within the particle. In addition, optical methods of particle analysis, such as nephelometry and flow cytometry, employ either an incandescent or a laser light source for measuring light scatter and light absorption of the particle. These and other optical analysis techniques have evolved to yield qualitative and quantitative information on the size of the particle, its surface composition, its constituent elements and, in some applications, the concentration of its internal components, such as hemoglobin in red blood cells. Optical flow cytometry is capable of even more sophisticated cell analysis, including the use of immunological techniques for tagging unique cell structures and soluble cellular entities. Virtually all of these instruments are based on precise measurements of the electrical and optical properties of the biological particle.

Several challenges have confronted those seeking to take advantage of the many opportunities presented by these particle analyzer instruments. First, concomitant with the advent of these technologies, there has arisen a corresponding need for quality control. One of the first control products for monitoring the accuracy of particle analyzers utilized fresh whole human blood. Unfortunately, fresh human blood posed several disadvantages when used as a control: First, it was necessary that the particles within the blood be counted to establish a base reference value. This necessitated visual determinations by a technician using microscopy. Second, fresh blood was usable as a control for only a limited time, generally less than one day. Each day required the acquisition of a new fresh blood control which, in turn, meant daily reference counting. In addition, it was not possible to compare results between laboratories due to the limited shelf life of the material and inherent variances in control samples.

Preserved non-fresh blood controls were developed to overcome the disadvantages of fresh blood. Non-fresh blood controls have been derived from plastics and, more prevalently, adapted from both human and non-human blood cells. The non-human components of blood control products typically utilize blood cells from selected animals which closely approximate the size and other features of the particle to be assayed, such as human leukocyte subpopulations. Because biological particles, in general, and leukocyte subpopulations, in particular, vary significantly in size, these non-human cell control products must utilize cells from several different animals to create analogs for the individual subpopulations. The size of the analogs must account for changes in the native leukocyte as the result of chemical insult, such as treatment by detergents or hypotonicity, which remove non-leukocyte particles from the sample and prepare the leukocyte analog for specific unique particle analysis procedures. As can be readily appreciated, this results in a complex composition utilizing various animal cells, each requiring particularized treatment to create a control product for the desired biological particle which, in turn, must be treated for the specific instrument to be utilized.

Medical science notwithstanding, there are also numerous industrial endeavors requiring precise particle analysis. There is a growing use of particle analysis in industry for the manufacture of non-medical products such as cosmetics, textiles and the like. Existing instruments for analyzing these products similarly examine the electronic and optical features of the product's constituent particles. These applications also require quality control to ensure the manufacture of the highest quality goods achievable. There is a corresponding deficiency in these industrial arts for a suitable method for designing custom particles for use as control products for these applications.

SUMMARY OF THE INVENTION

It is therefore a primary object of the present invention to provide a composition and a method for using the composition which allows for the precise manipulation of the electrical and optical properties of particles to achieve target values for those properties for use in connection with particle analyzers.

It is another object of the present invention to provide a composition and a method for using the composition for manipulating the electronic and optical properties of biological particles to create analogs for selected biological particles for use as control products for particle analyzers.

It is a related object of the present invention to provide a composition for the manipulation of the electrical and optical properties of a particle to achieve target values for those properties for use in industrial and other non-medical applications.

It is still another object of the present invention to provide a composition and a method for using the composition for the adaptation of biological particles to create analogs for human leukocyte subpopulations for use as control products for particle analyzers which differentiate among the primary human leukocyte subpopulations.

More particularly, it is an object of the present invention to provide a composition and a method for using the composition for the creation of human leukocyte subpopulation analogs for use as control products with differentiating particle analyzer instruments, such as instruments with Coulter VCS™ technology, utilizing few sources of base biological materials and, in most cases, a single source of base biological material.

It is yet a further object of the present invention to provide a composition and a method for using the composition for creating extended shelf life leukocyte subpopulation analogs for use as control products with differentiating particle analyzers, which utilize a single source of biological material and require only a few common and inexpensive components.

To accomplish these and other related objects, the present invention relates to a composition and a method for using the composition for manipulating the electrical and optical properties of particles. The composition generally comprises an ionic hypotonic buffering solution, a polyhydroxy alcohol, a stabilizing agent, and, in some applications, a non-ionic surfactant. By varying the relative concentrations of these components and by adjusting the timing of their combination and interaction, the composition and method for using the composition allow for the alteration of the electrical and optical properties of the particles to achieve target values for the properties. In one particularly advantageous application, the composition and method for using the composition of the invention allow for the creation of a plurality of analogs for the subpopulations of human leukocytes from a single biological particle for use as a control product in differentiating particle analyzers.

DESCRIPTION OF THE PREFERRED EMBODIMENT

The preferred embodiment of the composition of the present invention generally includes four chemical components: an ionic hypotonic buffered solution, a polyhydroxy alcohol, a stabilizing agent and, in some applications, a non-ionic surfactant. The composition also utilizes a base biological particle. The method of utilizing the composition of the invention involves adjusting the concentration of its constituent chemical components and the timing of their combination and interaction to achieve target electrical and optical values for the particle.

The preferred ionic hypotonic buffered solution includes saline and organic buffer having inorganic salts. A ringers solution may be modified to create the buffered solution. Most preferably, this modified ringers solution has a pKa of about 6–9 and an osmolarity of about 230 mOsml. The preferred buffer of the solution is MOPES, 3-(N-Morpholino) Propane-Sulfonic Acid. Other suitable buffers include TRIS, HEPES, citrate, phosphate and bicarbonate. The preferred formulation of the buffered solution contains 6.5 g/L sodium chloride, 0.14/L potassium chloride and 2.09 g/L MOPES.

The preferred polyhydroxy alcohol is propylene glycol. Propylene glycol is a well known compound typically used as a tissue penetrating agent for the cryopreservation of blood cells and as a co-solvent for numerous pharmaceuticals, cosmetics and processed foods. When applied to red blood cells, propylene glycol has been discovered to dramatically alter the electronic and optical properties of the treated cells. Treatment is characterized by the release of hemoglobin from the cell. The direct current measurement of volume may be increased or decreased beyond that observed with hypoosmotic or hyperosmotic saline solutions. Propylene glycol has also been found to freely pass the cell membrane barrier. It is an effective vehicle for the introduction or loss of molecules into or from cells, respectively. While propylene glycol is preferred, other polyhydroxylated alcohols may also prove effective in connection with the present composition. It has been found that ethylene glycol and dimethoxysulfoxide perform suitably well within the composition.

The ionic hypotonic buffered solution is combined with the polyhydroxy alcohol to form a preincubation media solution. The polyhydroxy alcohol may be present in the preincubation media at a concentration of about 1% to about 20% by volume. It is foreseeable that concentrations of polyhydroxy alcohol greater than 20% may be utilized, but diminished performance may be expected. Preferably, the polyhydroxy alcohol will be present at a concentration of about 5% to about 15% by volume. Most preferably, the polyhydroxy alcohol will be present at a concentration of about 10% by volume.

The preferred stabilizing agent of the present invention is glutaraldehyde. Variable concentrations of the stabilizing agent control the efflux of soluble intracellular components from the particle and the influx of the alcohol, surfactant and water into the particle. An increase in concentration of the stabilizing agent increases the light scatter and the conductance of the particle. The stabilizing agent also increases the osmolarity of the buffered solution and the alcohol to reduce particle volume. While glutaraldehyde is preferred, it is to be understood that other agents, such as formaldehyde, carbohydrozine, pyruvic aldehyde, potassium chromate and osmium tetroxide are also suitable stabilizing agents.

The concentration of stabilizing agent in the composition in the initial primary fixation phase is generally less than 5% by volume. The concentration of stabilizing agent in the secondary fixation phase, if needed for the desired application, is from one to over hundred times the concentration of stabilizing agent in the primary fixation phase. In the tertiary fixation phase, if needed for desired application, the concentration of stabilizing agent in the composition is from one to over one thousand times the concentration of stabilizing agent in the primary fixation phase. Preferably, the stabilizing agent is present in the composition during the primary fixation phase at a concentration ranging from about 0.00625% to about 4% by volume. In the secondary and tertiary fixation phases, if utilized, the concentration of stabilizing agent in the composition may range from about 0.00625% to about 25% by volume. The forgoing concentrations are based upon the utilization of a 100% solution of the stabilizing agent. It is to be understood that diluted formulations are within the scope of the present invention, particularly in the case of commercially available stock solutions of the stabilizing agent.

The composition of the present invention may also utilize, in some applications, a non-ionic surfactant to further manipulate the electronic and optical profiles of the particles. The non-ionic surfactant is required to produce a particle with high electronically measured volume, low light scatter and low conductivity as measured on a Coulter VCS™ instrument. The surfactant alters cell constituents to clarify the particle and modify the particle refractive index. The preferred non-ionic surfactant of the invention is Tergitol- 15™.

The non-ionic surfactant may be present in the composition at a concentration of about 0.01% to about 0.2% by volume. Preferably, the non-ionic surfactant will be present at a concentration of about 0.03%.

The composition of the present invention requires a base biological particle which, in most cases, constitutes biological cells. Non-human blood cells are preferred. Suitable non-human cells include alligator red blood cells, turkey red blood cells, shark red blood cells and goat red blood cells. In addition, single cells from dissociated tissue and small tissue fragments are also suitable biological particles for the composition. It is to be understood that the optimum base biological particle varies according to the desired target values of optical and electrical properties to be achieved. Inherent natural values of the properties of the base particle, such as its natural optical and electrical properties or size, may afford greater suitability for a desired result based on the proximity of the natural values of the properties to the target values.

The base biological particles are suspended in the buffered solution at a count of between about 0.25 to $1.5\times10^6/\mu L$. The preferred count is generally about $0.4\times10^6/\mu L$;

Certain applications for the composition of the present invention utilize a quench solution. This quench solution is a salt additive which prevents the biological particles from flocculating. The quench also assists in controlling volume, light scatter, and conductance. The quench may contain a single organic salt, but preferably includes a mixture of sodium carbonate, sodium chloride and sodium sulfate. The preferred combination includes about 15 g/L sodium carbonate, approximately 7 g/L sodium chloride and approximately 32 g/L sodium sulfate. The quench typically has a pH from about 9 to about 13 and an osmolarity from about 900 to about 1 ,100 mOsmol.

tion can bring about reproducible changes in the particle's electronic and optical profiles, as measured by selected particle analyzers. For instance, particle volume is determined by these instruments by analyzing the impedance and light scatter values of the particle. By adjusting the composition components in a prescribed manner, one may craft a desired range of impedance and light scatter for the particle and, hence, create a different measured volume. Similarly, internal and surface features of a particle are generally measured by analyzing the particle's radio frequency, opacity and light scatter. The present composition allows for the manipulation of these properties by adjusting the concentration of the composition's components and their sequence and timing of interaction. Specifically, the composition and method of the present invention allow one to adapt the electrical and optical properties of a particle to approximate those of another particle. The composition and method for using the composition of the present invention afford the ability to custom design a particle with desired internal and surface features, as perceived by radio frequency, opacity and light scatter measurements. The composition and method of the present invention also allow for the manipulation of other physical parameters of the particle, including particle shape and deformability.

Table 1 illustrates three parameters of measurements of a particle analyzer that can be manipulated with the composition of the present invention. As the table illustrates, a selected measurement parameter can be altered by changing component concentration and timing of interaction. The parameter alteration results in a different perceived value for certain properties of the particle.

TABLE 1

General Overview of Parameters Measured by Particle Analyzers Which Are Capable of Manipulation Using the Present Composition

| Parameter | Target Value | Method to Achieve Target Value |
|---|---|---|
| Impedance | Increase | Decrease osmolarity of buffered solution by approximately 60% and fix with 0.125% to 2% glutaraldehyde. Alternatively, incubate with polyhydroxy alcohol. |
| | Decrease | Increase concentration of buffered solution in primary and/or secondary fixation. Add tertiary fixation step. |
| Conductance | Increase | Increase glutaraldehyde concentration. |
| | Decrease | Preincubate in propylene glycol with or without surfactant. Fix with low glutaraldehyde concentration for several minutes. Fix again with 10–100 fold increase in glutaraldehyde concentration. |
| Light Scatter | Increase | Increase glutaraldehyde concentration. |
| | Modest Decrease | Preincubate in propylene glycol. Fix with low glutaraldehyde concentration. Progressively increase glutaraldehyde. |
| | Aggressive Decrease | Preincubate in propylene glycol and non-ionic surfactant. Fix with very low glutaraldehyde concentration. Progressively increase glutaraldehyde. |

The quench will generally be used in small amounts in the composition of the present invention. Generally, only from about 5 milliliters to 20 milliliters of the quench solution will be required to perform its function. Most preferably, 8 to 12 milliliters of quench will be used.

It has been unexpectedly found that subtle variations in the relative concentrations of the chemical components of the composition, together with changes in their combination and timing of interaction, effect significant modifications in the electrical and optical profiles of the base particle. It has been discovered that selected concentrations of the components and carefully followed procedures for their combina- The degree of manipulation of the properties of a selected particle varies according to the specific particle analyzer being used. Particle size based on electrical resistance may be larger on one instrument than another instrument because of the relative differences in instrument aperture size, flow rate and the type of diluting fluid. In addition, light scatter may vary based on the wave length, angle of light scatter and reagent specificity of the specific instrument.

This variance in particle property measurement manifests itself in the ultimate product. This is perhaps best illustrated in the context of human leukocyte analog preparation. A particle that measures as a human neutrophil analog on the Coulter MAXM™ analyzer may appear as a mononuclear cell on a TOA NE-8000™ instrument. If a Coulter MAXM™ neutrophil analog is prepared to be slightly larger in volume and with altered radio frequency and light scatter properties, the particle will behave as a mononuclear cell on a Technicon H-1™ instrument and as a neutrophil on the TOA NE-8000™. The composition of the present invention has allowed the preparation of a number of analogs on various instruments: (a) four types of analogs for the Coulter VCS™ instruments (b) three types for the TOA NE-8000™, (c) two for the Abbott Cell-Dyne™ 3000 and 3500 series, (d) two for the Technicon H-1™ hematology instruments, and (e) two particles for 3-part instruments, such as the Coulter Model S Plus IV™. It is anticipated that other analogs will be available for formulation using the present invention after sufficient experimentation and refinement of the composition.

A method of using the composition for producing human leukocyte subpopulation analogs utilizing a single base biological particle is outlined below. Representative procedures for creating individual subpopulation analogs are described in the examples. It is to be understood that the scope of the subject invention is not limited to creating such analogs, but extends to the manipulation of the electrical and optical properties of a biological particle to achieve target values of such properties, as measured by selected particle analyzers. This manipulation affords a broad scope of applications, one of which is the creation of human leukocyte analogs.

Large animal red blood cells are the preferred base biological particles for creating human leukocyte subpopulation analogs. The animals from which the preferred red blood cells may be harvested include those from the phyla Amphibia, Reptilia, Pices, and Chondrithes. The most preferred red blood cells are from the phyla Reptilia and, more particularly, from alligators. It is to be understood that red blood cells from other animals may also prove useful in creating human leukocyte subpopulation analogs, including animals from the phyla of Aves and Mammalia.

The preferred alligator red blood cells are initially collected in an anticoagulant containing Alsever's solution, with citrate, at a pH of between 6 and 7 and an osmolarity of 300 to 360 mOsmol. The collected cells may be stored up to 30 days if refrigerated.

The cells must be washed from the anticoagulant with the ionic hypotonic buffered solution. The purpose of washing the cells is to remove all or nearly all of the serum proteins from the cells that may interfere with the electronic and optical profiles of the cells. It has been found that contaminating serum proteins can also substantially affect light scatter and conductance values. The washed alligator cells may be stored in the wash solution for up to 72 hours, but must be later rewashed in the buffered solution to remove residual free hemoglobin from the supernatant fluid.

The washed cells are then preincubated in the preincubation media. Preincubation may continue for 5 to 45 minutes, depending on the resultant analog to be produced. The non-ionic surfactant may be employed with the preincubation media to create certain leukocyte analogs, discussed in greater detail below. If the surfactant is used during preincubation, the cells must be later washed to prevent flocculation.

The cells are next suspended in a primary weak fixative solution containing the stabilizing agent. Alternatively, the fixative solution may be added directly to the preincubation media. If added to the preincubation media, incubation should continue for an additional 30 minutes to 10 hours depending on the requirements of the final stabilized analog.

A secondary fixation phase is required to form certain analogs, such as the Coulter MAXM™ lymphocyte type I analog. The fixative solution in the secondary fixation phase includes a 10 to 100-fold increase in the concentration of the stabilizing agent to preserve the electronic and physical attributes of the cell. This secondary fixation may take place from one to five days. In the case of forming monocyte analogs for the Coulter VCS™ instruments, this step will also bring about a change in cell volume, conductance and light scatter resulting in a particle that is similar to the native monocyte.

A tertiary fixation phase is also utilized to create certain analogs, such as the Coulter MAXM™ mononuclear cell analog. The tertiary fixation requires a 100 to 1,000-fold increase in stabilizing agent concentration relative to the primary fixation phase. In the case where lymphocyte analogs are to be created, such a high fixative concentration will reduce the measured volume of the particle with minor changes in conductance and little or no change in light scatter. Further treatment at temperatures between 50 and 60 degrees Centigrade will continue the changes observed by utilizing high concentrations of the stabilizing agent.

Timing is critical during the first 15 to 60 minutes of the primary fixation phase. For instance, it is possible to fix cells for 30 minutes in a very low concentration of glutaraldehyde to lock in specific parameters in light scatter, volume and conductance. A ten-fold increase in glutaraldehyde concentration in the secondary fixation phase will have a reduced effect on particle properties as compared to the primary fixation phase. Consequently, as the cell becomes more "fixed," the stabilizing agent will have a progressively reduced effect on the particle.

The cells will be washed after the last fixation step. The preferred buffered solution may be used to wash the cells utilizing centrifugation methods of a type well known in the art. If the particular application requires, the cells may be washed and suspended in water.

The following examples follow the generic procedure outlined above. These examples are illustrative of the results achievable with the present composition in creating specific leukocyte subpopulation analogs. All examples utilize alligator red blood cells which have been washed in a saline solution and stored for less than 24 hours. Unless otherwise noted, the ionic buffered solution is diluted in deionized water to a concentration of 60% by volume. In addition, the glutaraldehyde solution used in the examples is a commercially available stock solution at a concentration of about 25% by volume, which is the preferred formulation of glutaraldehyde.

EXAMPLE NO. 1

Coulter MAXM™ Lymphocyte Type I Analog

The composition of the present invention may be utilized to prepare lymphocyte type I analogs for analysis by the Coulter MAXM™ instrument using the following procedure:

Components (a) Alligator red blood cells suspended in the buffered solution at a count of $0.40\pm0.15\times10^{6}/\mu L$;

(b) A preincubation media solution containing 10% propylene glycol and 90% of the buffered solution;

(c) A primary fixation media having a 0.3% of the glutaraldehyde solution in the buffered solution; and (d) A secondary fixation media having a 30% of the glutaraldehyde solution in the buffered solution.

Procedure

Using the components outlined above, 60 milliliters of fresh washed alligator red blood cells is then added to a one liter centrifuge bottle. 120 milliliters of the preincubation media solution is added to the bottle. The combined solution is gently inverted three to four times and incubated for 10 to 15 minutes. 720 milliliters of the primary fixation media is then added to the mixture and the combined mixture is incubated for an additional 15 minutes. After incubation, the mixture is centrifuged at 2,000 RPM for 6 to 8 minutes.

After centrifugation, the supernatant liquid is removed and the mixture is resuspended with 900 milliliters of the secondary fixation media. The contents are then resuspended by gentle mixing. The solution is incubated overnight at room temperature.

The cells are then washed with the buffered solution and centrifuged at 1,000 rpm for six minutes. The supernatant liquid is removed and the cells are washed two more times. After washing, the cells are suspended in a suitable suspending fluid of the type well-known to those in the art.

EXAMPLE NO. 2

Coulter MAXM™ Mononuclear Cell Analogs

The composition of the present invention may be utilized to prepare mononuclear cell analogs for analysis by the Coulter MAXM™ instrument using the following procedure.

Components (a) Alligator red blood cells suspended in the buffered solution to a count of 0.5 to $1.5\times10^6/\mu L$;

(b) A preincubation media containing 10% propylene glycol, 90% of the buffered solution, and 0.03% of Tergitol-15™;

(c) A primary fixation media having a 0.1% of the glutaraldehyde solution in water;

(d) A secondary fixation media having a 1% of the glutaraldehyde solution in water.

(f) A tertiary fixation media having a 30% concentration of the glutaraldehyde solution in water.

Procedure

Using the components outlined above, five milliliters of alligator red blood cells is first added to a 50 milliliter centrifuge tube. Five milliliters of the preincubation media is rapidly poured over the cells and is mixed by gentle swirling. The mixture is allowed to incubate at room temperature for 10 minutes and then centrifuged for one minute. A light salmon colored supernatant liquid will be formed. The supernatant liquid should be completely removed without disturbing the packed cells.

The buffered solution is rapidly added into the tube up to the 50 milliliter mark. The contents are mixed and incubated for five minutes and then centrifuged for two minutes. A cherry red supernatant liquid will be formed. The supernatant liquid should be completely removed without disturbing the packed cells. The primary fixation media is then added to the tube to the 50 milliliter mark. The cells are resuspended by gentle mixing and allowed to fix for 30 minutes at room temperature. The suspension should have faint red appearance.

The contents are then centrifuged for two and one half minutes and the supernatant liquid is removed. The contents are then resuspended with a secondary fixation media. The contents are then allowed to fix overnight at room temperature.

The cells are then resuspended using a vortex style mixer and the contents again centrifuged for one and one half minutes. The supernatant liquid is removed.

A tertiary fixation solution is then added to the contents of the tube. The contents are allowed to fix overnight. The cells are then resuspended by vortex mixing and the contents are centrifuged for one and a half minutes. The supernatant liquid is removed and the buffered solution is added to wash the contents. This washing procedure is repeated two more times. The supernatant liquid is removed and the cells are then suspended in a suitable suspending fluid.

EXAMPLE NO. 3

NE-8000™-Neutrophil Analogs (low eosinophil)

The composition of the present invention may be utilized to prepare neutrophil analogs for analysis by the NE-8000™ instrument using the following procedure.

Components (a) Alligator red blood cells suspended in the buffered solution to a count of 0.25 to $0.5\times10^6/\mu L$;

(b) A primary fixation media having a 1.0% of the glutaraldehyde solution in water and a 2.0% concentration of the quench solution; and (c) A secondary fixation media having a 15% of the glutaraldehyde solution in the buffered solution.

Procedure

Using the components outlined above, 18 milliliters of alligator red blood cells is added to a one liter plastic centrifuge bottle. 900 milliliters of the primary fixation media is rapidly poured over the cells and allowed to fix overnight. The supernatant liquid is then removed and 900 milliliters of the secondary fixation media is added. The combined solution is allowed to fix for one to four days at room temperature.

The supernatant liquid is then removed and 900 milliliters of the buffered solution is added. The contents are centrifuged and the supernatant liquid is removed. This washing procedure is then repeated at least two times. The cells are then transferred to a single 50 milliliter tube and suspended in a suitable suspending fluid.

EXAMPLE NO. 4

Coulter MAXM™ Neutrophil Analog

The composition of the present invention may be utilized to prepare neutrophil analogs for analysis by the Coulter MAXM™ instrument using the following procedure.

Components (a) Alligator red blood cells suspended in the buffered solution to a count of 0.25 to $0.5\times10^6/\mu L$;

(b) A preincubation media having 10% propylene glycol in the buffered solution;

(c) A primary fixation media having 2% of the glutaraldehyde solution in water;

(d) A quench reagent with an osmolarity of 1000 and a pH of 11.0; and (e) A secondary fixation media having 15% of the glutaraldehyde solution in the buffered solution.

Procedure

Using the components outlined above, 18 milliliters of the alligator cells is added to a one liter plastic centrifuge bottle. Approximately 80 milliliters of the preincubation media is poured rapidly over the cells and mixed by gentle swirling. The mixture is incubated at room temperature for 15 minutes. 808 milliliters of the primary fixation solution is rapidly poured into the mixture. After allowing 10–30 minutes to fix, nine milliliters of quench reagent is added and rapidly mixed by inverting the bottle 10 to 15 times. The combined solution is allowed to fix overnight at room temperature.

The supernatant liquid is then removed and a secondary fixation media is added. This mixture is also allowed to fix overnight. The supernatant is again removed and 150 milliliters of the buffered solution is added to resuspend the fixed cells. The suspended cells are transferred to four 50 milliliters centrifuge tubes and centrifuged for one minute. The supernatant liquid is removed and the cells are washed at least two times the buffered solution. The cells are then suspended in a suitable suspension fluid.

EXAMPLE NO. 5

NE-8000™-Neutrophil Analogs (high eosinophil)

The composition of the present invention may be utilized to prepare neutrophil analogs for analysis by the NE-8000 instrument using the following procedure.

Components (a) Alligator red blood cells suspended in the buffered solution to a count of 0.25 to $0.5\times10^6/\mu L$;

(b) A preincubation media containing 10% propylene glycol and 90% of the buffered solution;

(c) A primary fixation media containing a 1% of the glutaraldehyde solution in water;

(d) A secondary fixation media containing a 15% of the glutaraldehyde solution in the buffered solution; and (e) A quench solution having an osmolarity of 1000 and a pH of 11.0.

Procedure

Using the components outlined above, add 16 milliliters of alligator red blood cells to a one liter plastic centrifuge bottle. 80 milliliters of the preincubation media is rapidly poured over the cells and mixed by gentle swirling. The mixture is allowed to incubate at room temperature for 10–30 minutes.

Following incubation, 808 milliliters of the primary fixation solution is added to the preincubation mixture. After allowing one hour to fix, eight milliliters of the quench reagent is added and the bottle is inverted 10 to 15 times. The combined solution is allowed to fix at room temperature overnight.

The supernatant liquid is then removed and 900 milliliters of the secondary fixation media is added. This solution is allowed to fix from one to four days at room temperature.

The supernatant liquid is then removed and 50 milliliters of the buffered solution is added. The suspended cells are transferred to 50 milliliter sterile centrifuge tubes and centrifuged for one minute. The supernatant liquid is removed and the cells are washed at least two times. The cells are transferred to a single 50 milliliter tube and suspended in a suitable suspending fluid.

EXAMPLE NO. 6

NE-8000™ Lymphocyte Analogs

The composition of the present invention may be utilized to prepare lymphocyte analogs for analysis by the NE-8000 instrument using the following procedure.

Components (a) Alligator red blood cells suspended in the buffered solution to a count of 0.25 to $0.5\times10^6/\mu L$;

(b) A preincubation media having about 10% propylene glycol, with about 90% of the buffered solution and 0.03% of Tergitol-15™;

(c) A primary fixation media having 40% of the glutaraldehyde solution in the buffered solution.

Procedure

Using the components outlined above, add 90 milliliters of alligator red blood cells to a one liter centrifuge bottle. 180 milliliters of the preincubation media is rapidly poured over the cells and mixed by gentle swirling. The solution is allowed to incubate at room temperature for 10 to30 minutes.

The contents are centrifuged at 2,000 rpm for 10 to 12 minutes. The supernatant is removed and 900 milliliters of the buffered solution is added to the bottle and allowed to set for 5 minutes. The contents are then centrifuged at 2,000 rpm for 10 to 12 minutes.

The supernatant liquid is removed and 900 milliliters of the primary fixation media is added. The cells are resuspended by gentle mixing and allowed to fix for one to four days at room temperature. The suspended cells should have a salmon-colored appearance.

After fixation, the light brown supernatant liquid is removed and buffered solution is added. The suspended cells are then transferred to 50 milliliter centrifuge tubes and centrifuged for three minutes. The supernatant liquid is then removed and the cells are washed at least three times. The cells are then suspended in a suitable suspending fluid.

The foregoing examples are illustrative of the leukocyte analogs that can be prepared utilizing the composition of the present invention. Various instruments can be accommodated by altering components, component concentration and combination.

The present invention provides a simple composition and method for using the composition to manipulate optical and electrical properties of cells to achieve target values for those properties. The present invention allows for the adaptation of the electrical and optical properties of a biological particle to approximate the values of those properties of another particle. Utilizing only a few components and readily available instruments, the optical and electrical properties of biological particles can be crafted to obtain desired values for the properties as measured by a particle analyzer.

The specific application of the invention to create leukocyte subpopulation analogs is a significant stride in the art of hematology. The present invention overcomes previous shortcomings in the art by utilizing a blood control having a shelf life of at least 30 days. The control can be prepared and utilized repeatedly over the course of its shelf life. The results of an analysis using the present composition can be readily compared with the results of another laboratory also using the composition because the same control product can be used by both labs, thereby providing identical reference values.

The present invention also provides significant advantages over non-human blood controls existing in the art. The present composition generally utilizes a single base biological particle not numerous particles. By varying the component concentration and adjusting the time of the components' combination and interaction, the single biological particle can be adapted for almost any leukocyte subpopulation analog. This invention eliminates the need to retain stockpiles of assorted animal cells to create a suitable analog for use with a particular instrument. Instead, this composition allows for the flexible adaptation of a single biological particle to fit the desired analog or desired instrument. This is a simple and inexpensive composition that can be utilized by any lab technician. The present invention not only promotes greater ease in control development and utilization, but also clearly advances the interests of accurate diagnoses and efficacious treatment utilizing this technology.

It is apparent from the foregoing that this invention is well-adapted to obtain all the ends and objectives set forth above along with other advantages which are obvious to the invention.

It is to be understood that certain features and subcombinations are useful and may be employed without reference to other features and subcombinations. This is contemplated by the disclosure and is within the scope of the claims.

Because many possible embodiments may be made of the present invention without departing from its scope, it is further understood that all matters set forth herein are to be interpreted as illustrative only, and not in a limiting sense.

The following is claimed:

1. A composition for altering the optical and electrical properties of a red blood cell, the composition comprising:

at least one red blood cell having hemoglobin therein and having optical properties and electrical properties at respective natural values;

a hypotonic buffered solution;

a polyhydroxy alcohol for leaking a quantity of the hemoglobin from the red blood cell; and a stabilizing agent for fixing the cell having had the quantity of its hemoglobin released;

wherein the hypotonic buffered solution, the polyhydroxy alcohol and the stabilizing agent are present in the composition at selected respective concentrations to alter the natural values of the optical and electrical properties of the cell to achieve selected target values of the optical and electrical properties.

2. The composition of claim 1 wherein the polyhydroxy alcohol is propylene glycol.

3. The composition of claim 2 wherein the propylene glycol is present in the composition at a concentration from about 1% to about 20% by volume.

4. The composition of claim 3 wherein the stabilizing agent is glutaraldehyde.

5. The composition of claim 4 wherein the glutaraldehyde is present in the composition at a concentration from about 0.00625% to about 4% by volume.

6. The composition of claim 1 further comprising a non-ionic surfactant at a sufficient concentration to alter the respective natural values of the optical and electrical properties of the cell to achieve the selected target values of the optical and electrical properties.

7. The composition of claim 6 wherein the non-ionic surfactant is present in the composition at a concentration from about 0.01% to about 0.2% by volume.

8. The composition of claim 7 wherein the red blood cell includes a plurarlity of alligator red blood cells.

9. The composition of claim 8 wherein the alligator red blood cells are present in the composition at a count of 0.25 to $1.5 \times 10^6/\mu L$.

10. A composition for altering the optical and electrical properties of a red blood cell, the composition comprising:

at least one red blood cell having hemoglobin therein and having optical and electrical properties at respective natural values;

a preincubation media comprising a hypotonic buffered solution and a polyhydroxy alcohol, the polyhydroxy alcohol being present in the media at a concentration from about 1% to about 20% by volume for leaking a quantity of the hemoglobin from the red blood cell; and a stabilizing agent at a concentration from about 0.00625% to about 4% by volume for fixing the red blood cell having had the quantity of its hemoglobin released;

wherein the preincubation media and stabilizing agent are present in the composition at selected respective concentrations to alter the respective natural values of the optical and electrical properties of the cell to achieve selected target values of the optical and electrical properties.

11. The composition of claim 10 wherein the polyhydroxy alcohol is propylene glycol.

12. The composition of claim 11 wherein the propylene glycol is present in the composition at a concentration of about 10% by volume.

13. The composition of claim 12 wherein the stabilizing agent is glutaraldehyde.

14. The composition of claim 13 wherein the glutaraldehyde is present in the composition at a concentration from about 0.0125% to about 2% by volume.

15. The composition of claim 12 wherein the glutaraldehyde is present in the composition at a concentration from about 0.05% to about 2% by volume.

16. The composition of claim 13 further comprising a non-ionic surfactant.

17. The composition of claim 16 wherein the non-ionic surfactant is present in the composition at a concentration of about 0.03% by volume.

18. The composition of claim 17 wherein the red blood cell is a plurality of alligator red blood cells.

19. A method of manipulating the optical and electrical properties of a biological particle to achieve selected target values for the respective properties, the method comprising:

providing a base biological particle having both optical and electrical properties at respective natural values;

contacting the particle with a preincubation media, the media including a hypotonic buffered solution and a polyhydroxy alcohol at selected respective concentrations to manipulate the optical and electrical properties of the particle;

allowing the particle to remain in contact with the preincubation media for an incubation time;

contacting the particle with a primary fixative solution after the step of contacting the particle with the preincubation media, the fixative solution including a stabilizing agent at a selected primary concentration to manipulate the optical and electrical properties of the particle;

allowing the particle to remain in contact with the primary fixative solution for a first period of time; and removing the particle from the primary fixative solution;

wherein the incubation time and the first period of time are selected to manipulate the respective natural values of the optical and electrical properties of the particle to achieve the selected target values for the optical and electrical properties.

20. The method of claim 19 further comprising the step of contacting the particle with a secondary fixative solution, wherein the secondary fixative solution includes the stabilizing agent at a secondary concentration equal to about one to about one hundred times the primary concentration.

21. The method of claim 20 further comprising the step of allowing the particle to remain in contact with the secondary fixative solution for a second period of time.

22. The method of claim 21 wherein the second period of time is selected to manipulate the optical and electrical properties of the particle from the natural values of the respective properties to the selected target values for the respective properties.

23. The method of claim 22 further comprising the step of contacting the particle with a tertiary fixative solution, wherein the tertiary fixative solution includes the stabilizing agent at a tertiary concentration equal to about one to about one thousand times the primary concentration.

24. The method of claim 23 further comprising the step of allowing the particle to remain in contact with the tertiary fixative solution for a third period of time.

25. The method of claim 24 wherein by the third period of time is selected to manipulate the optical and electrical properties of the particle from the natural values of the respective properties to the selected target values for the respective properties.

26. The method of claim 19 wherein the step of contacting the particle with the preincubation media includes the step of contacting the particle with a non-ionic surfactant.

27. The method of claim 19 further comprising the steps of washing the particle between each successive step.

28. The method of claim 27 wherein each washing step includes washing the particle with a wash solution, centrifuging the particle and the wash solution to form a supernatant liquid and decanting the supernatant liquid.

29. A method of manipulating the optical and electrical properties of an animal cell to achieve selected target values for the respective properties, the method comprising:

providing an animal red blood cell having optical and electrical properties at respective natural values;

contacting the cell with a preincubation media, the media including a hypotonic buffered solution and propylene glycol, the propylene glycol being present in the media at a selected concentration from about 1% to about 20% by volume;

allowing the cell to remain in the preincubation media for an incubation time from about 5 minutes to about 45 minutes;

contacting the cell with a primary fixative solution after the step of contacting the cell with the preincubation media, the primary fixative solution including glutaraldehyde at a selected primary concentration from about 0.00625% to about 4% by volume;

allowing the cell to remain in the primary fixative solution for a first period of time from about 15 minutes to 24 hours; and removing the cell from the primary fixative solution;

wherein the incubation time and the first period of time are selected to manipulate the optical and electrical properties of the cell from the natural values of the respective properties to the target values for the respective properties.

30. The method of claim 29 further comprising the step of contacting the cell with a secondary fixative solution, wherein the secondary fixative solution includes glutaraldehyde at a secondary concentration from about 0.00625% to about 25% by volume.

31. The method of claim 30 further comprising the step of allowing the cell to remain in contact with the secondary fixative solution for a second period of time.

32. The method of claim 31 wherein the second period of time is selected to manipulate the optical and electrical properties of the cell from the natural values of the respective properties to the target values for the respective properties.

33. The method of claim 32 further comprising the step of contacting the cell with a tertiary fixative solution, wherein the tertiary fixative solution includes glutaraldehyde at a tertiary concentration from about 0.00625% to about 25% by volume.

34. The method of claim 33 further comprising the step of allowing the cell to remain in contact with the tertiary fixative solution for a third period of time.

35. The method of claim 34 wherein the third period of time is selected to manipulate the optical and electrical properties of the cell from the natural values of the respective properties to the target values for the respective properties.

36. The method of claim 35 wherein the step of contacting the cell with the preincubation media includes the step of contacting the particle with a non-ionic surfactant.

37. The method of claim 36 further comprising the steps of washing the cell between each successive step.

38. The method of claim 37 wherein each washing step includes washing the cell with a wash fluid, centrifuging the cell and the wash fluid to form a supernatant liquid, and decanting the supernatant liquid.

39. A composition for altering the optical and electrical properties of a red blood cell to create an analog for a human leukocyte subpopulation for use as a control product for a differentiating particle analyzer instrument, the composition comprising:

at least one red blood cell having hemoglobin therein and having optical and electrical properties at respective natural values;

a hypotonic buffered solution;

a polyhydroxy alcohol for leaking a quantity of the hemoglobin from the red blood cell; and a stabilizing agent for fixing the red blood cell having had the quantity of its hemoglobin released;

wherein the hypotonic buffered solution, the polyhydroxy alcohol and the stabilizing agent are present in the composition at selected respective concentrations to manipulate the natural values of the optical and electrical properties of the cell to approximate values of optical and electrical properties of the human leukocyte subpopulation, as measured by the particle analyzer instrument.

40. The composition of claim 39 wherein the polyhydroxy alcohol is propylene glycol.

41. The composition of claim 40 wherein the propylene glycol is present in the composition at a concentration from about 1% to about 20% by volume.

42. The composition of claim 39 wherein the stabilizing agent is glutaraldehyde.

43. The composition of claim 42 wherein the glutaraldehyde is present in the composition at a concentration from about 0.00625% to about 4% by volume.

44. The composition of claim 39 further comprising a non-ionic surfactant at a sufficient concentration to manipulate the natural values of the optical and electrical properties of the cell to approximate the values of the optical and electrical properties of the human leukocyte subpopulation.

45. The composition of claim 44 wherein the non-ionic surfactant is present in the composition at a concentration from about 0.01% to about 0.05% by volume.

46. The composition of claim 45 wherein the red blood cell is a plurality of alligator red blood cells.

47. The composition of claim 46 wherein the alligator red blood cells are present in the composition at a count of 0.25 to $1.5\times10^6/\mu L$.

48. A method of manipulating the optical and electrical properties of a biological particle to create an analog for a human leukocyte subpopulation for use as a control product on a differentiating particle analyzer instrument, the method comprising:

providing a base biological particle having optical and electrical properties at respective natural values;

contacting the particle with a preincubation media, the media including a hypotonic buffered solution and a polyhydroxy alcohol at selected respective concentrations to manipulate the optical and electrical properties of the particle;

allowing the particle to remain in contact with the preincubation media for an incubation time;

contacting the particle with a primary fixative solution after the step of contacting the particle with a preincubation media, the primary fixative solution including a stabilizing agent at a selected primary concentration to manipulate the optical and electrical properties of the particle;

allowing the particle to remain in contact with the fixative solution for a first period of time; and removing the particle from the fixative solution;

wherein the incubation time and the first period of time are selected to manipulate the natural values of the optical and electrical properties of the particle to approximate values of optical and electrical properties of the human leukocyte subpopulation, as measured by the particle analyzer instrument.

49. The method of claim 48 further comprising the step of contacting the particle with a secondary fixative solution, wherein the secondary fixative solution includes the stabilizing agent at a secondary concentration equal to about one to about one hundred times the primary concentration.

50. The method of claim 49 further comprising the step of allowing the particle to remain in contact with the secondary fixative solution for a second period of time.

51. The method of claim 50 wherein the second period of time is selected to manipulate the optical and electrical properties of the particle from the natural values of the respective properties to approximate the values for the optical and electrical properties of the human leukocyte subpopulation.

52. The method of claim 51 further comprising the step of contacting the particle with a tertiary fixative solution, wherein the tertiary fixative solution includes the stabilizing agent at a tertiary concentration equal to about one to about one thousand times the primary concentration.

53. The method of claim 52 further comprising the step of allowing the particle to remain in contact with the tertiary fixative solution for a third period of time.

54. The method of claim 53 wherein the third period of time is selected to manipulate the optical and electrical properties of the particle from the natural values of the respective properties to approximate the values for the optical and electrical properties of the human leukocyte subpopulation.

55. The method of claim 48 wherein the step of contacting the particle with the preincubation media includes the step of contacting the particle with a non-ionic surfactant.

56. The method of claim 48 further comprising the steps of washing the particle between each successive step.

57. The method of claim 56 wherein each washing step includes washing the particle with a wash solution, centrifuging the particle and the wash solution to form a supernatant liquid, and decanting the supernatant liquid.

58. An analog for a human leukocyte subpopulation for use as a control product on a differentiating particle analyzer instrument, the analog created by the process comprising:

providing a base biological particle having both optical and electrical properties at respective natural values;

contacting the particle with a preincubation media, the media including a hypotonic buffered solution and a polyhydroxy alcohol at selected respective concentrations to manipulate the optical and electrical properties of the particle;

allowing the particle to remain in contact with the preincubation media for an incubation time;

contacting the particle with a primary fixative solution after the step of contacting the particle with the preincubation media, the fixative solution including a stabilizing agent at a selected primary concentration to manipulate the optical and electrical properties of the particle;

allowing the particle to remain in contact with the primary fixative solution for a first period of time; and removing the particle from the primary fixative solution;

wherein the incubation time and the first period of time are selected to manipulate the respective natural values of the optical and electrical properties of the particle to achieve the selected target values for the optical and electrical properties.

* * * * *